US011896873B2

(12) United States Patent
Williams et al.

(10) Patent No.: US 11,896,873 B2
(45) Date of Patent: Feb. 13, 2024

(54) CARDIOVASCULAR EXERCISE DEVICE, SYSTEM AND METHOD

(71) Applicant: Mark Williams, Reading (GB)

(72) Inventors: Mark Williams, Reading (GB); Chris Flynn, Bristol (GB)

(73) Assignee: Mark Williams, Reading (GB)

( * ) Notice: Subject to any disclaimer, the term of this patent is extended or adjusted under 35 U.S.C. 154(b) by 179 days.

(21) Appl. No.: 17/633,857

(22) PCT Filed: Mar. 12, 2021

(86) PCT No.: PCT/GB2021/051139
§ 371 (c)(1),
(2) Date: Feb. 8, 2022

(87) PCT Pub. No.: WO2022/043647
PCT Pub. Date: Mar. 3, 2022

(65) Prior Publication Data
US 2022/0266092 A1    Aug. 25, 2022

(30) Foreign Application Priority Data

Aug. 24, 2020   (GB) ..................................... 2013171

(51) Int. Cl.
*A63B 24/00*   (2006.01)
*A63B 22/00*   (2006.01)

(52) U.S. Cl.
CPC ...... *A63B 24/0075* (2013.01); *A63B 24/0062* (2013.01); *A63B 2022/0092* (2013.01); *A63B 2225/50* (2013.01)

(58) Field of Classification Search
CPC ............ A63B 69/0028; A63B 24/0062; A63B 71/0686; A63B 24/0075;
(Continued)

(56) References Cited

U.S. PATENT DOCUMENTS 277,241 A * 5/1883 Day ...................... H01H 37/76
                                                200/535
3,846,704 A * 11/1974 Bessette ............. A61B 5/02416
                                                377/5
(Continued)

FOREIGN PATENT DOCUMENTS

CN          105457250 A     4/2016

OTHER PUBLICATIONS

United Kingdom Intellectual Property Office, Search Report in United Kingdom Patent Application No. GB2013171.0, 1 p. (Jan. 27, 2021).
European Patent Office, International Search Report in International Patent Application No. PCT/GB2021/051139, 1 p. (Aug. 9, 2021).

*Primary Examiner* — Garrett K Atkinson
(74) *Attorney, Agent, or Firm* — Leydig, Voit & Mayer, Ltd.

(57) ABSTRACT

A cardiovascular exercise device is provided. The cardiovascular exercise device is for use to administer an exercise program including shuttle runs. The cardiovascular exercise device includes: a tower placeable at a first location; a user input associated with the tower; a pacing bar arranged to display a target pace of a user for a shuttle run of a track distance from the first location; and a processor configured to operate an exercise program. The administration of the exercise program includes the steps of: receiving a signal from the user input; defining a repetition as the time between subsequent signals from the user input; and indicating pacing information to the user based upon this signal.

22 Claims, 4 Drawing Sheets

(58) Field of Classification Search
CPC .... A63B 2024/0009; A63B 2024/0025; A63B 2024/0056; A63B 2024/0068; A63B 2024/0078; A63B 2024/0093; A63B 2102/14; A63B 2102/22; A63B 2208/12; A63B 2220/89; A63B 2225/10; A63B 2225/50; A63B 2230/06; A63B 2230/30; A63B 2243/0025; A63B 2022/0092; A63B 24/0087; A63B 71/023; A63B 71/0622; A63B 2024/0065; A63B 2071/0625; A63B 2071/0627; A63B 2071/063; A63B 2071/0658; A63B 2071/0675; A63B 2071/0694; A63B 2214/00; A63B 2220/17; A63B 2220/62; A63B 2220/801; A63B 2220/803; A63B 2220/833; A63B 2225/15; A63B 2225/20; A63B 2225/54; A63B 2225/74; A63B 2230/00; A63B 2230/40; A63B 69/00; A63B 22/00; A63B 24/00; G07C 1/22; G16H 20/30

See application file for complete search history.

(56) References Cited

U.S. PATENT DOCUMENTS

| | | | | |
|---|---|---|---|---|
| 4,823,367 | A * | 4/1989 | Kreutzfeld | A63B 71/0686 |
| | | | | 377/5 |
| 8,628,333 | B2 * | 1/2014 | Prinzel, III | A63B 71/06 |
| | | | | 434/247 |
| 11,484,767 | B2 * | 11/2022 | Marcus | G06M 3/06 |
| 2003/0087220 | A1 * | 5/2003 | Bessette | A63B 69/0028 |
| | | | | 434/247 |
| 2008/0280730 | A1 | 11/2008 | Alexanderson | |
| 2012/0091921 | A1 * | 4/2012 | Buresta | A63B 69/12 |
| | | | | 315/320 |
| 2014/0277241 | A1 * | 9/2014 | Bleich | A61N 1/36585 |
| | | | | 607/18 |
| 2015/0335950 | A1 * | 11/2015 | Eder | A63B 22/0605 |
| | | | | 482/8 |
| 2015/0335951 | A1 * | 11/2015 | Eder | G16H 30/20 |
| | | | | 482/8 |
| 2017/0087437 | A1 * | 3/2017 | Vonada | G16H 20/30 |
| 2021/0370133 | A1 * | 12/2021 | LaPoint | A63B 24/0021 |
| 2021/0379447 | A1 * | 12/2021 | Lee | A63B 24/0075 |

* cited by examiner

CARDIOVASCULAR EXERCISE DEVICE, SYSTEM AND METHOD

CROSS-REFERENCE TO RELATED APPLICATIONS

This application is a national phase application of International Patent Application No. PCT/GB2021/051139, filed May 12, 2021, which claims priority to United Kingdom Patent Application No. GB 2013171.0, filed Aug. 24, 2020, both of which are incorporated by reference herein in their entireties for all purposes.

BACKGROUND

The present application relates to a cardiovascular exercise device, system and method.

Cardiovascular exercise (also known as aerobic exercise or cardio) is a common form of exercise for health and fitness. This typically includes running, jogging, swimming, cycling and walking.

One particular form of cardiovascular exercise is shuttle runs. That is, a series of runs back and forth between two points. Each run between the two points is labelled a repetition. Shuttle runs such as these form the basis of the multi-stage fitness test (also known as the beep test, bleep test, PACER test, PACER (Progressive Aerobic Cardiovascular Endurance Run), Yo-Yo test, or the 20 metre Shuttle Run Test (20 m SRT)). The test is used to determine or estimate an athlete's aerobic capacity.

The multi-stage fitness test is a running test, in which a test subject runs between first and second positions to another before a timed beep sounds. The timed beep indicates the time at which the test subject must reach the line. The test subject continues running back and forth between the first and second positions, reaching the position before the beep each time. As the test continues, the time between consecutive beeps gets shorter and hence the test subject must run at a faster pace. Once the test subject can no longer reach the position before the beep, the maximum level which they were successful in reaching the position is recorded as their result for the test. In certain testing regimes, a test subject may be allowed to miss one or two beeps before their test is complete.

In the original test regime, two points which are 20 metres apart are selected. Alternative distances may be used as required by space constraints. The timing between initial consecutive beeps is selected such that a speed of 8.5 km/h is required to be on the pace of the beeps. For example, at 20 metres the initial time between beeps may be 8.47059 seconds. The required speed then increases by 0.5 km/h each minute (roughly, taking into account the time needed to have an integer number of repetitions). Each time the speed increases, the "level" of the test increases by 1. A score for the multi-stage fitness test is then determined as the last level at which the test subject was able to meet the pace of the beeps.

Aerobic capacity may be measured, for example as maximal oxygen consumption (also known as $VO_2$ max, maximal oxygen uptake, peak oxygen uptake or maximal aerobic capacity).

$VO_2$ max is formally defined using the Fick Equation (1), with values obtained during an exertion at maximum effort:

$$VO_2 \text{ max} = Q \times (C_aO_2 - C_vO_2) \quad (1)$$

Where Q is the cardiac output of the heart, $C_aO_2$ is the arterial oxygen content, and $C_vO_2$ is the venous oxygen content. In practice, it is difficult to calculate this precisely as it requires a subject to exert maximum effort, which may be dangerous for those with impaired cardiovascular systems, or impractical for others.

The multi-stage fitness test represents a suitable method for estimating $VO_2$ max. This may be estimated from a multi-stage fitness test score via published tables such as Ramsbottom, R. et al, 1988, "A progressive shuttle run test to estimate maximal oxygen uptake", *British Journal of Sports Medicine*, 22(4), pp.141-144. Alternatively, $VO_2$ max can be estimated from a multi-stage fitness test score based upon a calculation such as Flouris, A., 2005, "Enhancing the efficacy of the 20 m multistage shuttle run test", *British Journal of Sports Medicine*, 39(3), pp.166-170, reproduced as Equation (2):

$$VO_2 \text{ max} = (v \times 6.65 - 35.8) \times 0.95 + 0.182 \quad (2)$$

Where v is the velocity required for the level reached in km/h.

Generally, the multi-stage fitness test is performed using a recording of beeps played over a speaker. However, it is difficult to ensure that test subjects are meeting the required pace with such a system. Furthermore, the test subject is merely provided with a number indicating the level that they reached. This is not the clearest indication of fitness level as it may depend upon the characteristics of the testing regime used.

Such shuttle runs can also be used to form the basis of many other exercise programs and regimes. This may include, for example, high-intensity interval training (HIIT).

GB 2 477 912 A discloses a system to monitor the performance of an exercise using wireless tags. One particular exercise is a bleep test, where the user runs between first and second pods and checks in with their RFID card. In this manner, the system can administer a bleep test. However, the user is not aware of how they are doing during the test, besides whether they make the beeps or not. As they must also scan the RFID card on each trip, this makes it significantly harder to administer an effective and reliable test.

There is therefore a need for an improved cardiovascular exercise device, system and method.

CN 105457250 A discloses a shuttle run guiding system which comprises a host and a guiding device corresponding to a runway.

US 2017/087437 A1 discloses an exercise pacing device including multiple lights that are configured to be placed at regular intervals along a running track.

US 2012/091921 A1 discloses a system for light signalling to supply a moving light reference to an athlete.

SUMMARY

A cardiovascular exercise device for training shuttle runs is provided according to claim 1.

This device allows a user to easily and effectively take a multi-stage fitness test and ensure they keep up with the pacing using the pacing bar. The pacing bar allows the user to be aware of their pacing before any beeps in the traditional test which are only provided too late for the repetition. As the known multi-stage fitness test simply uses a beep when the user should be at either end point, this often means that the user uses too much energy early on in the exercise as their pace is too quick. Alternatively, the complete opposite may happen and they fall behind the intended pace. The device provides continual pacing information.

The complete dependence of the prior art on using an audio beep means you have to use it in a quiet environment (unlike a commercial gym which may be noisy). The present invention can use visual indications to avoid this. Furthermore, all users must start their exercise program at the same time otherwise they would not know which beep is relevant to them. The present invention can provide visual cues which allow multiple exercise programs to be carried out on different devices in an area.

Furthermore, the device can also be used to replace traditional exercise equipment such as treadmills and/or exercise bicycles (or any static training device). With such static devices there is no literal finish line for the user. As a result, they are naturally less motivated during their running. This may especially be the case when they are reaching the end of their exercise program. With the present device, there is a fixed point in space the user is running to which they can use for greater motivation and hence performance.

The device may also be used for any other suitable exercise program incorporating repetitions (shuttle runs) where pacing information may be displayed.

The track distance may be selectable, and the processor may be arranged to adjust the pacing bar based upon the selected track distance. This allows the distance for each repetition to be selected, with the target time being adjusted. Particularly, the timing or pacing of the pacing bar may be adjusted by the processor. As such the cardiovascular exercise device can be easily used as a self-contained and adjustable unit that does not require significant additional infrastructure in order to operate. That is, a single cardiovascular exercise device (or a pair thereof) can be set up effectively anywhere simply by placing the tower(s), selecting the distance and carrying out the exercise. The same device(s) can then be taken to a second location and this can be repeated, potentially with a different distance. This means that the cardiovascular exercise device is a truly portable and convenient device which can be readily used in a variety of applications.

The track distance may be selectable from a number of discrete values. The track distance may be selectable as multiples of 5 metres or 5 yards. Typical values for multi-stage fitness tests or other exercise programs may be one or more of 10, 15, 20 or 25 metres or one or more of 10, 15, 20 or 25 yards, so making these easily selectable improves the ease of use of the device.

The pacing information may be an audio signal or a visual signal. This allows the user to easily know whether they have met the target pace for a repetition.

Visual signals may be particularly preferable as the cardiovascular exercise device can be used with the volume in "mute" (i.e. not making any noises). This allows the cardiovascular exercise device to be more easily used in a noisy environment such as a busy gym. This can also allow multiple cardiovascular exercise devices with different starting points to be used at the same time. This can also provide feedback to indicate whether the user is ahead of or behind the target pace.

The processor may be configured to determine whether the user is behind the target pace for a repetition based upon the signal from the user input and terminate the exercise program when a threshold number of repetitions are behind the target pace. This automatically completes the exercise once the user can no longer keep up with the pace.

The threshold number of repetitions may be a consecutive threshold of repetitions. This means the user can miss a certain number of repetitions without the test ending, provided that they can catch up to the required pace.

The processor may be configured to calculate an indication of the user's fitness based at least in part upon a number of repetitions completed and convey this to the user. This allows the user to quickly and effectively understand the context of their multi-stage fitness test score or performance in another exercise program.

The indication of the user's fitness may be maximal oxygen consumption. This may also be known as $VO_2$ max. $VO_2$ max is a useful measure of fitness which can be tracked over time to see improvements.

The cardiovascular exercise device may be freely moveable. This allows the device to be moved between locations, such as gyms or sports halls, to carry out multi-stage fitness tests or other exercise program in many locations using the same device.

The cardiovascular exercise device may further comprise a wireless communications unit for communicating with a further cardiovascular exercise device or user device. The user device may be a mobile phone, or fitness device such as a smart watch. In this sense, the user can be provided with data relating to their multi-stage fitness test or other exercise program, such as their score or $VO_2$ max.

The pacing bar may indicate a start part and an end point, and a target position of the user between the start part and end point. This easily allows the user to understand the information regarding the pacing.

The exercise program may further comprise a rest period between shuttle runs, and the pacing bar may be further arranged to indicate a length of time of the rest period. Many exercise programs include rest periods between repetitions. It is advantageous for the cardiovascular exercise device to further indicate these rest periods to the user to allow them to recover appropriately.

The cardiovascular exercise device may further comprise a battery unit for powering the cardiovascular exercise device. A battery unit allows the cardiovascular exercise device to be easily moved between locations.

The pacing bar may be arranged on the tower. This makes it easy to transport the cardiovascular exercise device and carry out a multi-stage fitness test or other exercise program.

The processor may be configured to: determine an identity of the user based upon the user input. The identity of the user may be used to automatically configure their preferred parameters for the multi-stage fitness test or other exercise program. The identity of the user may be used to track changes in the performance of the user over time in multi-stage fitness tests or other exercise programs.

The user input may be arranged on the tower. The cardiovascular exercise device may be more easily moveable.

The user input may comprise first and second user inputs arranged on an upper and lower part of the tower respectively. This can introduce additional aspects into a workout, such as requiring the user to interact with different inputs at different points, such as during alternate repetitions.

The user input may be one or more of: a push-button; a touch capacitor; a pressure sensing mat; a motion sensor; a proximity capacitor; and/or a wireless communication sensor configured to detect the presence of a user device. These are particularly suitable user inputs for the cardiovascular exercise device.

Each cardiovascular exercise system allows a user to easily and effectively take a multi-stage fitness test or other exercise program and ensure they keep up with the pacing using the pacing bar. The pacing bar allows the user to be aware of their pacing before any beeps in the traditional test which are only provided too late for the repetition.

The at least one pacing bar may be arranged on the tower of the first cardiovascular exercise device or the tower of the second cardiovascular exercise device. This makes it easy to transport the cardiovascular exercise system and carry out a multi-stage fitness test or other exercise program.

Each cardiovascular exercise device may comprise at least one pacing bar arranged to display a target pace of a user for a shuttle run of the tower distance. With a pacing bar associated with each cardiovascular exercise device, the user can track their pacing when they are running a repetition in either direction, when a single pacing bar may difficult to view in both directions of running.

Each cardiovascular exercise device may also be useable as a single device, in order to carry out an exercise program on its own as described in the present specification.

The first and second cardiovascular exercise devices may be in communication with each other. For example, via Bluetooth or Wi-Fi. This allows the devices to transmit signals therebetween in order to monitor the progress of the user in the multi-stage fitness test or other exercise program.

The first and second cardiovascular exercise devices may be arranged a tower distance from one another as start and end points for a shuttle run of the tower distance. This may allow the user to effectively perform a multi-stage fitness test or other exercise program.

The first and/or second cardiovascular exercise devices may be freely moveable to define the tower distance, the processor may be arranged to adjust the pacing bar based upon the selected tower distance. This allows the cardiovascular exercise devices to be placed at appropriate locations for the parameters desired for a particular multi-stage fitness test or other exercise program.

The tower distance may be selectable, the processor arranged to adjust the pacing bar based upon the selected tower distance. Particularly, the timing or pacing of the pacing bar may be adjusted by the processor. As such the cardiovascular exercise devices can be easily used as a self-contained and adjustable system that does not require significant additional infrastructure in order to operate. That is, the pair of cardiovascular exercise devices can be set up effectively anywhere simply by placing the towers, selecting the distance and carrying out the exercise. The same devices can then be taken to a second location and this can be repeated, potentially with a different distance. This means that the cardiovascular exercise devices are a truly portable and convenient system which can be readily used in a variety of applications.

The tower distance may be selectable from a number of discrete values. The tower distance may be selectable as multiples of 5 metres or 5 yards. Typical values for multi-stage fitness tests or other exercise programs may include one or more of 10, 15, 20 or 25 metres or one or more of 10, 15, 20 or 25 yards, so making these easily selectable improves the ease of use of the device. 15 or 20 metres may be the most typical distance for a multi-stage fitness test or other exercise program.

This method allows a user to easily and effectively take a multi-stage fitness test or other exercise program. The method may be provided commercially by an organiser of a multi-stage fitness test or other exercise program.

BRIEF DESCRIPTION OF THE DRAWINGS

The present description will be made with reference to the accompanying Figures, in which.

DETAILED DESCRIPTION OF THE DRAWINGS

Figure 1:
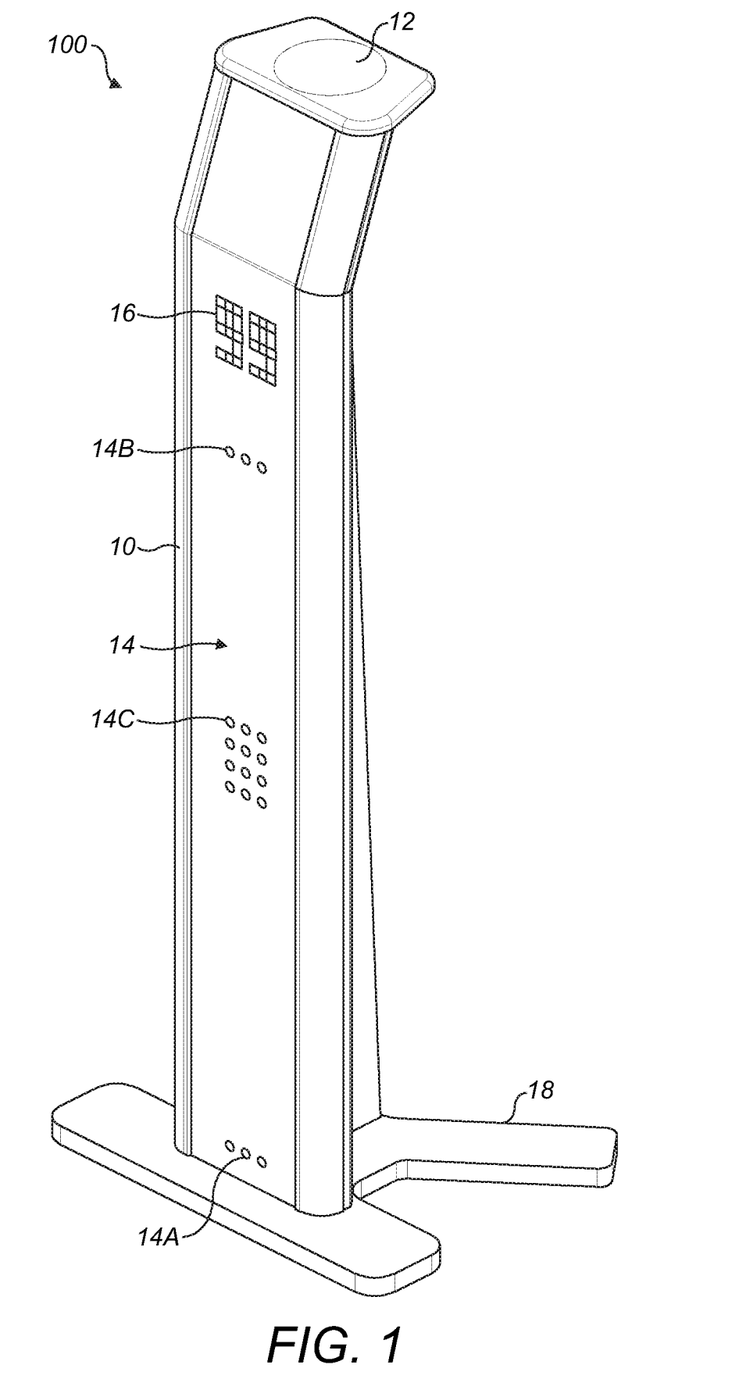
FIG. 1 shows a cardiovascular exercise device in a perspective view.
Figure 2:
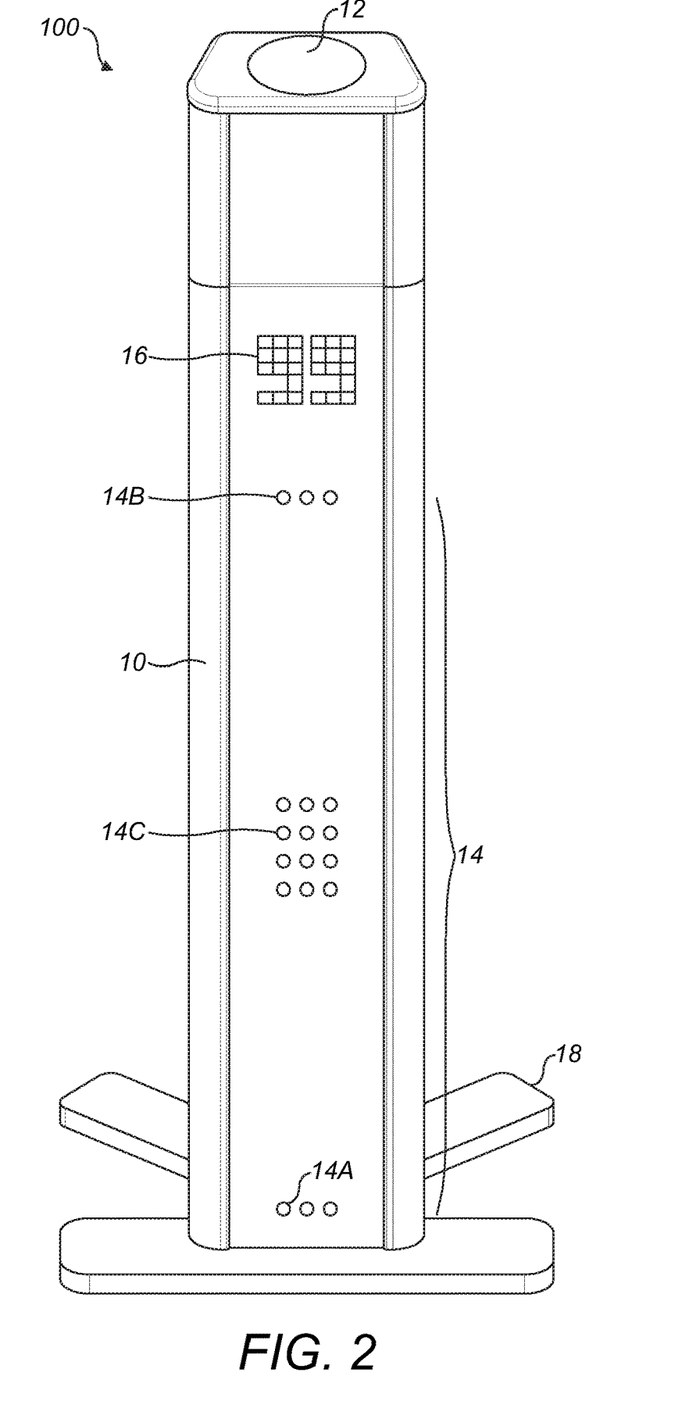
FIG. 2 shows a front view of the cardiovascular exercise device of FIG. 1.
Figure 3:
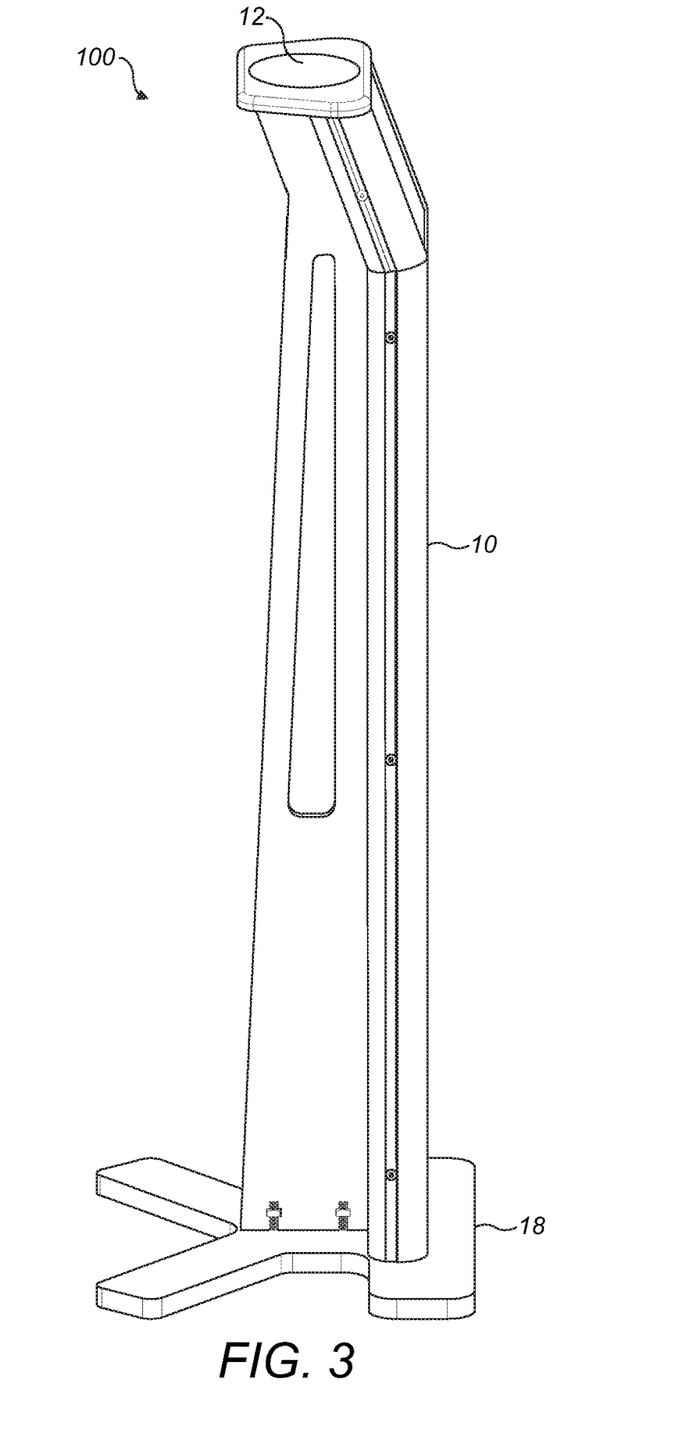
FIG. 3 shows a side view of the cardiovascular exercise device of FIG. 1.

A cardiovascular exercise device 100 is shown in FIGS. 1 to 3. The cardiovascular exercise device 100 is useable to carry out a multi-stage fitness test or other exercise program including a number of shuttle run repetitions. While the present description is in relation to a multi-stage fitness test, the cardiovascular exercise device 100 may be used for any fitness workout that involves a series of movements back and forth between two points, such as a beep test, Bronco test, or any other exercise program.

The cardiovascular exercise device 100 comprises a tower 10 and is positionable at a location. The location that the cardiovascular exercise device 100 is located represents a first position in the multi-stage fitness test or other exercise program. This first position may be a start position for the multi-stage fitness test or other exercise program.

The tower 10 and hence the cardiovascular exercise device 100 may be a fixed installation, that is not moveable without disassembly or destruction. Alternatively, it may be freely moveable such that it can be placed in a first location, be used to carry out a multi-stage fitness test or other exercise program, and then moved to another location and used to carry out another multi-stage fitness test. This or other exercise program may be useful, for example, if the device is moved between different sports halls or gyms. The cardiovascular exercised device 100 may also be used in an outdoor environment such as a park or running track. The cardiovascular exercise device 100 may be freestanding. The cardiovascular exercise device 100 may include one or more legs or supports 18 that support the tower 10.

The cardiovascular exercise device 100 may have a permanent power supply. Alternatively, the cardiovascular exercise device 100 may be powered by a battery unit. The battery unit may be rechargeable. The cardiovascular exercise device 100 may include energy generation means such as solar panels arranged to charge the battery.

The cardiovascular exercise device 100 comprises a user input 12. The user input 12 may be a single user input, such as a single button. Alternatively, the user input 12 may include a number of individual buttons, touchscreens, or other input devices. The user input 12 generates and outputs a signal when the user 20 interacts therewith. The cardiovascular exercise device 100 may further comprise a display 16 which may be used for the selection of an exercise program, and/or to display information to a user 20 of the cardiovascular exercise device 100.

For example, information displayed to the user 20 may include feedback on their exercise, such as one or more of: the level they are currently on; an indication of when to start, rest or stop; and/or an indication of the user's fitness as discussed below.

The user input 12 may be one or more of: a push-button; a touch capacitor; a pressure sensing mat; a motion sensor;

a proximity capacitor; and/or a wireless communication sensor configured to detect the presence of a user device. A pressure sensing mat may detect when the user 20 has stepped on it as the interaction from the user 20. Thus, the user 20 does not need to take any additional action that they would not naturally take while running. A motion sensor may detect the presence of a user 20, for example by them waving their hand or leg over the sensor. A wireless communication sensor may be, for example, a Bluetooth or RFID sensor which detects a remote device of the user 20, such as a RFID card, smart phone, or other fitness accessory such as a smartwatch.

The user input 12 may comprises first and second user inputs arranged on an upper and lower part of the tower 10 respectively. This may allow the user 20 to vary their exercise regime, for example, the user 20 may alternate between interacting with the upper and lower user inputs to engage further muscles during their routine.

The user input 12 may be used to select or start an exercise program on a processor of the cardiovascular exercise device 100. The processor may be a single processing unit within the cardiovascular exercise device 100, or may be formed of multiple individual processing units in communication with one another. The processor receives the signal from the user input 12 when the user 20 interacts with the user input 12. The processor runs an exercise program when the user 20 interacts with the user input 12 to start a multi-stage fitness test or other exercise program. The user 20 may interact with the user input 12 during the exercise to indicate repetitions, and at the end of the exercise.

During the exercise program, the processor receives a signal from the user input 12 when the user reaches the cardiovascular exercise device 100 and interacts with the user input 12. A repetition is defined as the time between subsequent signals from the user input 12. In certain embodiments, the time between subsequent signals from the user input 12 may be defined as two repetitions—the shuttle run from the tower 10 and the shuttle run back to the tower 10. Pacing information is indicated to the user 20 based upon this signal. The pacing information may be in the form of beeps or other audible sounds typically used to indicate when a user 20 should have completed a repetition.

The pacing information is also conveyed to the user 20 via a pacing bar 14 as discussed in detail below. As a result, it may be that no audible pacing information is required. This allows the cardiovascular exercise device 100 to be operated in busy or noisy environments. There may also be multiple cardiovascular exercise devices 100 operating in close proximity, so the lack of audible indicators helps prevent confusion between multiple users 20.

The cardiovascular exercise device 100 may be able to operate a multi-stage fitness test or other exercise program over a number of different distances per repetition. The distance for a particular multi-stage fitness test or other exercise program may be selectable by a user 20 of the cardiovascular exercise device 100. The distance for a multi-stage fitness test or other exercise program may be referred to as the track distance or tower distance. The track distance defines the shuttle run for each repetition of the multi-stage fitness test or other exercise program.

The track distance may selectable from a number of discrete values, as opposed to infinitely adjustable distances. These discrete values may be, for example multiples of 5 metres or 5 yards. In particular embodiments, there may be a limited list of distances presented to the user 20, for example 10 metres, 15 metres and 20 metres (or 10 yards, 15 yards, 20 yards). Alternatively, the track distance may be selectable with more granularity, for example with 0.5 metre or 1 metre increments.

The track distance being selectable means that the track distance may be adjusted without having to replace the existing hardware and/or install additional hardware. Instead, the same cardiovascular exercise device 100 may be used and the track distance can be selected for use with this same cardiovascular exercise device 100.

Figure 4:
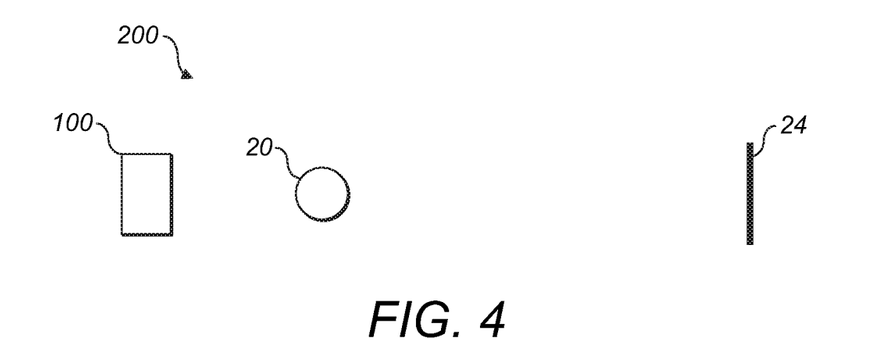
FIG. 4 shows a schematic top view of a cardiovascular exercise system with one cardiovascular exercise device.

In the simplest form, the cardiovascular exercise device 100 may be used as a cardiovascular exercise system as shown in FIG. 4. A single cardiovascular exercise device 100 is provided at a first location. A marker or indicator 24 is provided at a second location, spaced from the first location. The marker 24 may be a permanent marker such as a painted line on the ground. This may be useful if the cardiovascular exercise device 100 is fixed in location. Otherwise, the marker 24 may be a temporary marker such as a cone or flag. The marker 24 may be a natural element in the location of the cardiovascular exercise device 100, such as a tree. The track distance may be measured from the marker 24, and the cardiovascular exercise device 100 placed at an appropriate location.

The user 20 interacts with the cardiovascular exercise device 100 to start a multi-stage fitness test or other exercise program. The cardiovascular exercise device 100 may explain the rules to the user 20, for example via the display 16 or via a recorded message played over a loudspeaker. The loudspeaker may be built-in to the cardiovascular exercise device 100. The user 20 then begins the multi-stage fitness test or other exercise program by running to the marker 24, and back to the cardiovascular exercise device 100. The cardiovascular exercise device 100 may release an audible signal, such as a beep, to indicate the moment at which the user 20 should have reached the line 24, and/or the moment at which the user 20 should have returned to the cardiovascular exercise device 100. This information may be presented to the user via a pacing bar 14 as described in detail below.

Once the user 20 reaches the cardiovascular exercise device 100, they interact with the user input 12 to indicate that they have reached the cardiovascular exercise device 100. A repetition may be defined as the run between two interactions with the user input 12. Alternatively, this may define two repetitions—one repetition from the cardiovascular exercise device 100 to the marker 24 and one repetition from the marker 24 to the cardiovascular exercise device 100.

The processor of the cardiovascular exercise device 100 may receive a signal when the user input 12 is interacted with. The timing of the signal from the user input 12 can be compared to the time at which the user 20 should be at the cardiovascular exercise device 100 based upon the current level of the multi-stage fitness test or other exercise program in order to determine pacing information regarding the user 20. This pacing information may be, for example, that they are behind or ahead of the target pace. The target pace can be derived based upon the time allocated for each repetition and the track distance being used for the multi-stage fitness test or other exercise program. The pacing information may be conveyed to the user 20. This may be an audio signal or a visual signal. For example, the pacing information may be in the form of a beep sound as conventionally used in multi-stage fitness tests or other exercise program.

The cardiovascular exercise device 100 further comprises a pacing bar 14. The pacing bar 14 may be arranged on the tower 10 of the cardiovascular exercise device 100, or separate thereto. That is, the pacing bar 14 may be an integral component of the tower 10 of the cardiovascular exercise device 100. The pacing bar 14 is used to display information regarding the target pace to the user 20. In particular, the pacing bar 14 may comprise two markers 14A, 14B which indicate the two end locations of the multi-stage fitness test or other exercise program. The pacing bar 14 may then comprise a target marker 14C which moves between the two markers 14A, 14B to show the location at which the user 20 should be to run at the target pace. For example, the pacing bar 14 may be formed of an array of LEDs, or any other suitable system. As the multi-stage fitness test or other exercise program continues the target marker 14C will move back and forth between the two markers 14A, 14B to indicate the target pace, increasing in speed as the time allocated for each repetition reduces. The pacing bar 14 may be used to indicate the pacing information to the user 20. For example, the pacing bar 14 may flash when a repetition should be completed.

If the processor determines that the user 20 is behind the target pace—that is, the user 20 is reaching the cardiovascular exercise device 100 and interacting with the user input 12 after they should be (i.e. after the beep), this may be identified as a missed repetition. The number of missed repetitions may be compared to a threshold value and the multi-stage fitness test or other exercise program may be deemed complete once the number of missed repetitions exceeds the threshold value. For example, the threshold value may be for two missed repetitions. The threshold value may be defined in relation to consecutive missed repetitions. That is, the threshold value may be for example two consecutive missed repetitions. If the user 20 misses a single repetition, then achieves the next repetition according to the target pace they may be allowed to continue, regardless of the total number of missed repetitions. The threshold value may also be defined as a blended threshold value, such that the test is considered completed if X consecutive repetitions are missed, or Y total repetitions are missed. The threshold value may be selected by the user 20 at the start of their exercise program. In this sense the user 20 may set the difficulty of the exercise program.

The user 20 can be alerted that they have missed a repetition via the pacing bar 14 and/or via audible feedback. Accordingly, the user 20 is aware each time they have missed a repetition such that they know clearly when the exercise program is about to be terminated due to consecutive missed repetitions.

The pacing bar 14 may be used to indicate to the user when they should rest between repetitions and/or during an exercise program. In particular, if the exercise program includes one or more rest periods between repetitions (or shuttle runs). During these rest periods, the pacing bar 14 may count-down to indicate how long the rest period should be. In this sense, the pacing bar 14 can indicate a length of time for the rest period. For example, the pacing bar 14 may display an hour-glass style countdown of the rest period. That is, the entire pacing bar 14 may illuminate to indicate the start of the rest period. The pacing bar 14 may then begin to turn off sections of the pacing bar 14 in order from one end to another (such as top to bottom) as the rest period expires. Once the entire pacing bar 14 is turned off, this indicates that the rest period has finished and the next stage of the exercise program can begin.

In embodiments in which the track distance is selectable, or adjustable, the processor may adjust the pacing bar 14 based upon the selected track distance. That is, an overall size of the pacing bar 14 will not change as the cardiovascular exercise device 100 is not replaced. However, the movement of the pacing bar 14 may be adjusted. For example, if a current level of an exercise test requires the user to run at a given speed v, and a track distance d has been selected, the processor will adjust the pacing bar 14 such that the time for the target marker 14C to move between the end markers 14A, 14B is calculated as d/v. In this sense the processor adjusts the pacing bar 14 to account for differing track distances. The same pacing bar 14 (with no additions or alterations) can be used for different track distances.

In other words, the processor adjusts the timing or pacing of the pacing bar 14. This is without physically adjusting the pacing bar 14. This also differs from multi-lap counters or the like where a pacing bar 14 may simply repeat itself based upon the number of laps being carried out—such a pacing bar 14 would not be adjusted but instead would simply repeat itself.

Once the cardiovascular exercise device 100 has determined that the multi-stage fitness test or other exercise program has been completed, the processor may terminate the exercise program.

While the cardiovascular exercise device 100 has been described in detail with reference to a multi-stage fitness test, it may also be used for any other suitable exercise program involving a number of repetitions. In this sense, the cardiovascular exercise device 100 may be used as an alternative workout to existing static machines such as treadmills and/or exercise bicycles.

The processor may also calculate an indication of the user's fitness. This indication of the user's fitness may be their maximal oxygen consumption ($VO_2$ max) in accordance with Equation (2). The cardiovascular exercise device 100 may convey this indication of the user's fitness to the user 20. This may be, for example, via the display 16. Alternatively, or additionally, the cardiovascular exercise device 100 may transmit the indication of the user's fitness to a remote device such as user's mobile telephone for the user 20 to view. The cardiovascular exercise device 100 may transmit the indication of the user's fitness to a remote location, such as a server, which is accessible by the user 20.

The cardiovascular exercise device 100 may comprise a wireless communications unit. This unit may communicate with another cardiovascular exercise device, or with a user device such as a mobile phone, or fitness accessory such as a smartwatch.

The cardiovascular exercise device 100 may be able to determine an identity of the user 20, for example based upon the user input 12. This may be by the user 20 interacting with the user input 12 or cardiovascular exercise device 100 using a remote device which contains identifying data, such as via RFID or Bluetooth. The cardiovascular exercise device 100 may, via the processor, use the identification of the user 20 for one or more further aspects. For example, the user 20 may have preferences for the track distance for their multi-stage fitness test which the cardiovascular exercise device 100 may automatically select once the user 20 has been identified.

The identity of the user 20 can also be used to build a profile of the user 20. This profile may include, for example, a history of scores the user achieved on the multi-stage fitness test, or information derived therefrom such as $VO_2$ max. The current multi-stage fitness test score, or information derived therefrom, may be compared to this historical data to determine whether the user 20 is improving or not. With the user 20 identified, information regarding the multi-stage fitness test may be transmitted to a remote user device, such as a mobile phone, so that the user 20 can review the data. This remote device may be associated with the user 20 such that the cardiovascular exercise device 100 automatically transmits the information to the remote device once the multi-stage fitness test is completed.

Thus, a cardiovascular exercise device 100 for training shuttle runs is provided. The cardiovascular exercise device 100 comprises a tower 10 placeable at a first location and a user input 12 associated with the tower 10. This may be on or adjacent to the tower 10. A pacing bar 14 is provided, the pacing bar 14 arranged to display a target pace of a user 20 for a shuttle run of a track distance from the first location (i.e. from the tower). The cardiovascular exercise device 100 further includes a processor configured to operate an exercise program. The exercise program comprising the steps of: receiving a signal from the user input 12; defining a repetition as the time between subsequent signals from the user input 12; and indicate pacing information to the user 20 based upon this signal.

In this sense, the user 20 is able to use a single cardiovascular exercise device 100 to carry out a multi-stage fitness test and receive an indication of their fitness.

Figure 5:
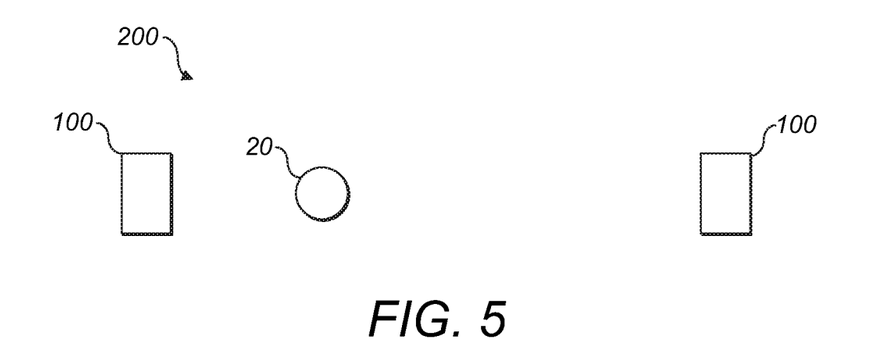
FIG. 5 shows a schematic top view of a further cardiovascular exercise system with two cardiovascular exercise devices.

An alternative cardiovascular exercise system 200 is shown in FIG. 5. This cardiovascular exercise system 200 comprises two cardiovascular exercise devices 100. The cardiovascular exercise devices 100 are spaced from one another by a tower distance. Any reference to the track distance above is equally applicable to the tower distance. The tower distance may be adjustable or selectable as described above. For example, one or both of the cardiovascular exercise devices 100 may be freely moveable to define a tower distance for a multi-stage fitness test. The tower distance is then the shuttle distance required for each repetition of the test.

The cardiovascular exercise devices 100 may be in communication with each other. This communication may be wired or wireless. For example, the cardiovascular exercise devices 100 may be in communication with each other via Bluetooth or Wi-Fi. The cardiovascular exercise devices 100 may be paired to one another in this sense.

The pair of cardiovascular exercise devices 100 used in the cardiovascular exercise system of FIG. 5 may each be as described above. Unless expressly specified otherwise, any aspects of the cardiovascular exercise device 100 noted above applied equally to the pair of cardiovascular exercise devices 100 used in the system 200 of FIG. 5.

Alternative cardiovascular exercise devices 100 may optionally be used in the system 200 of FIG. 5. For example, it may not be necessary for the cardiovascular exercise devices 100 to be capable of carrying out a multi-stage fitness test as a single cardiovascular exercise device 100. Likewise, there may be a single shared processor for the two cardiovascular exercise devices 100. Alternatively, each of the cardiovascular exercise devices 100 may include their own processor. Likewise, each cardiovascular exercise device 100 may include its own pacing bar 14. Alternatively, there may be a single pacing bar 14 provided. With the tower distance being selectable, the processor may adjust the or each pacing bar 14 in the same manner as discussed above in relation to the track distance.

To carry out the multi-stage fitness test, the user 20 may interact with the user input 12 on one of the cardiovascular exercise devices 100. One of the cardiovascular exercise devices 100 may be designated as a starting cardiovascular exercise device 100, and it may not be possible to start the multi-stage fitness test from the other cardiovascular exercise device 100. Alternatively, it may be possible to start the multi-stage fitness test from either of the cardiovascular exercise devices 100.

Once the multi-stage fitness test has been started at one of the cardiovascular exercise devices 100, the user 20 must run to the other of the cardiovascular exercise devices 100. Once they reach the other cardiovascular exercise device 100, the user 20 must interact with the user input 12 of that cardiovascular exercise device 100 to indicate that they have reached it. This distance between the two cardiovascular exercise devices 100 may be defined as one repetition. The user 20 then must run from the other cardiovascular exercise device 100 back to the starting cardiovascular exercise device 100 and interact with the user input 12 of the starting cardiovascular exercise device 100.

The processor(s) then act in the same way as the cardiovascular exercise system 200 of FIG. 4 to determine a number of missed repetitions. These missed repetitions are compared to the threshold value and the test is completed in the same manner as described above.

In this sense, the user 20 is able to use a pair of cardiovascular exercise devices 100 to carry out a multi-stage fitness test and receive an indication of their fitness.

Thus, a cardiovascular exercise system 200 is provided. The cardiovascular exercise system 200 may comprise first and second cardiovascular exercise devices 100 with the functionality described above.

A further cardiovascular exercise system 200 is also provided. The further cardiovascular exercise system 200 may comprise first and second cardiovascular exercise devices 100. Each of the cardiovascular exercise devices 100 may comprise a tower 10 placeable at a location, and a user input 12 associated with each tower 10. This may be on or adjacent to the tower 10. The first and second cardiovascular exercise devices 10 are placeable a tower distance away from one another. At least one pacing bar 14 is provided, arranged to display a target pace of a user 20 for a shuttle run of the tower distance. One or more processors are configured to operate an exercise program comprising the steps of: receiving a signal from the user input 12; defining a repetition as the time between subsequent signals from the user input 12; and indicating pacing information to the user 20 based upon this signal.

A method of cardiovascular exercise is provided. A cardiovascular exercise device 100 as described above may be provided. Alternatively, a cardiovascular exercise system 200 as described above may be provided. The exercise program is begun by the user 20. The user 20 then runs repetitions as defined above. A user input signal is received after each repetition (or each pair or repetitions, depending on how the repetitions are defined).

The method may comprise determining a measure of the user's fitness and conveying this to them, such as the maximal oxygen consumption discussed above. A target pace may be displayed to the user 20 via the pacing bar 14.

This method allows the user 20 to effectively determine a measure of their fitness using the cardiovascular exercise device 100 or cardiovascular exercise system 200 described above.

The invention claimed is:

1. A cardiovascular exercise device for an exercise program comprising shuttle runs, the cardiovascular exercise device comprising:
   a tower placeable at a first location;
   a user input associated with the tower;
   a pacing bar arranged to display a target pace of a user for
      a shuttle run of a track distance from the first location, a processor configured to operate an exercise program comprising the steps of:
  receiving a signal from the user input;
  defining a repetition as the time between subsequent signals from the user input; and
  indicating pacing information to the user based upon said signal,
wherein the track distance is selectable, and the processor is arranged to adjust the pacing bar based upon the selected track distance.

2. The cardiovascular exercise device of claim 1, wherein the track distance is selectable from a number of discrete values.

3. The cardiovascular exercise device of claim 1, wherein the processor is configured to determine whether the user is behind the target pace for a repetition based upon the signal from the user input and terminate the exercise program when a threshold number of repetitions are behind the target pace.

4. The cardiovascular exercise device of claim 3, wherein the threshold number of repetitions is a consecutive threshold of repetitions.

5. The cardiovascular exercise device of claim 1, wherein the processor is configured to calculate an indication of the user's fitness based at least in part upon a number of repetitions completed and convey this to the user.

6. The cardiovascular exercise device of claim 1, wherein the cardiovascular exercise device is freely moveable.

7. The cardiovascular exercise device of claim 1, further comprising a wireless communications unit for communicating with a further cardiovascular exercise device or user device.

8. The cardiovascular exercise device of claim 1, wherein the pacing bar indicates a start point and an end point of a repetition of the shuttle run, and a target position of the user between the start point and end point.

9. The cardiovascular exercise device of claim 1, wherein the exercise program further comprises a rest period between shuttle runs, the pacing bar further arranged to indicate a length of time of the rest period.

10. The cardiovascular exercise device of claim 1, wherein the pacing bar is arranged on the tower.

11. The cardiovascular exercise device of claim 1, wherein the processor is configured to:
  determine an identity of the user based upon the user input.

12. The cardiovascular exercise device of any preceding claim 1, wherein the user input is arranged on the tower.

13. The cardiovascular exercise device of claim 12, wherein the user input comprises first and second user inputs arranged on an upper and lower part of the tower respectively.

14. A cardiovascular exercise system comprising:
first and second cardiovascular exercise devices each according to claim 1, the first and second cardiovascular exercise devices placeable a tower distance away from one another for a shuttle run of the tower distance.

15. A cardiovascular exercise system comprising:
first and second cardiovascular exercise devices, each comprising:
  a tower placeable at a location;
  a user input associated with each tower,
  the first and second cardiovascular exercise devices placeable a tower distance away from one another;
  at least one pacing bar arranged to display a target pace of a user for a shuttle run of the tower distance,
  one or more processors configured to operate an exercise program comprising the steps of:
    receiving a signal from the user input;
    defining a repetition as the time between subsequent signals from the user input; and
    indicating pacing information to the user based upon said signal,
  wherein the tower distance is selectable, the one or more processors arranged to adjust the pacing bar based upon the selected tower distance.

16. The cardiovascular exercise system of claim 15, wherein the at least one pacing bar is arranged on the tower of the first cardiovascular exercise device or the tower of the second cardiovascular exercise device.

17. The cardiovascular exercise system of claim 15, wherein each cardiovascular exercise device comprises at least one pacing bar arranged to display a target pace of a user for a shuttle run of the tower distance.

18. The cardiovascular exercise system of claim 15, wherein the first and second cardiovascular exercise devices are in communication with each other.

19. The cardiovascular exercise system of claim 15, wherein the first and second cardiovascular exercise devices are arranged the tower distance from one another as start and end points for the shuttle run of the tower distance.

20. The cardiovascular exercise system of claim 15, wherein the first and/or second cardiovascular exercise devices are freely moveable to define the tower distance.

21. The cardiovascular exercise system of claim 15, wherein the tower distance is selectable from a number of discrete values.

22. A method of cardiovascular exercise comprising the steps of:
providing one or more cardiovascular exercise devices including:
  a tower placeable at a first location;
  a user input associated with the tower, wherein said cardiovascular exercise devices are placeable a tower distance away from one another when more than one cardiovascular exercise device is provided;
  at least one pacing bar arranged to display a target pace of a user for a shuttle run of at least one of the tower distance and a track distance from the first location,
  at least one processor configured to operate an exercise program comprising the steps of:
    receiving a signal from the user input; and
    defining a repetition as the time between subsequent signals from the user input;
    indicating pacing information to the user based upon said signal,
  wherein at least one of the tower distance and the track distance is selectable, and the at least one processor is arranged to adjust the pacing bar based upon at least one of the selected tower distance and the selected track distance;
beginning the exercise program; and
receiving a user input after each repetition.

* * * * *

UNITED STATES PATENT AND TRADEMARK OFFICE
CERTIFICATE OF CORRECTION

| | | |
|---|---|---|
| PATENT NO. | : 11,896,873 B2 | |
| APPLICATION NO. | : 17/633857 | |
| DATED | : February 13, 2024 | |
| INVENTOR(S) | : Mark Williams et al. | |

It is certified that error appears in the above-identified patent and that said Letters Patent is hereby corrected as shown below:

On the Title Page

At item (22), please delete "Mar. 12, 2021" and insert --May 12, 2021--

Signed and Sealed this
Fourteenth Day of May, 2024

Katherine Kelly Vidal
*Director of the United States Patent and Trademark Office*